United States Patent
Cantrell et al.

(10) Patent No.: US 7,498,434 B2
(45) Date of Patent: Mar. 3, 2009

(54) TWO-PHASE METHOD FOR THE SYNTHESIS OF SELECTED PYRAZOLOPYRIMIDINES

(75) Inventors: Gary Lee Cantrell, Troy, IL (US); Frank William Moser, Arnold, MO (US); Robert Edward Halvachs, Belleville, IL (US)

(73) Assignee: Mallinckrodt Inc, Hazelwood, MO (US)

( * ) Notice: Subject to any disclaimer, the term of this patent is extended or adjusted under 35 U.S.C. 154(b) by 203 days.

(21) Appl. No.: 10/585,006

(22) PCT Filed: Dec. 2, 2004

(86) PCT No.: PCT/US2004/040241

§ 371 (c)(1),
(2), (4) Date: Jun. 28, 2006

(87) PCT Pub. No.: WO2005/070931

PCT Pub. Date: Aug. 4, 2005

(65) Prior Publication Data

US 2007/0155995 A1    Jul. 5, 2007

Related U.S. Application Data

(60) Provisional application No. 60/536,302, filed on Jan. 14, 2004.

(51) Int. Cl.
*C07D 487/04* (2006.01)
*A61K 31/519* (2006.01)

(52) U.S. Cl. .................................. 544/282; 514/259.3

(58) Field of Classification Search ................ 544/262, 544/281, 282
See application file for complete search history.

(56) References Cited

U.S. PATENT DOCUMENTS

| 4,626,538 | A | 12/1986 | Dusza et al. |
| 5,714,607 | A | 2/1998 | Padmanathan |
| 6,399,621 | B1 | 6/2002 | Dusza et al. |
| 6,476,223 | B2 | 11/2002 | Tombari et al. |
| 6,852,858 | B2 | 2/2005 | Feher et al. |
| 2002/0072605 | A1 | 6/2002 | Tombari et al. |
| 2003/0040522 | A1 | 2/2003 | Korodi et al. |

FOREIGN PATENT DOCUMENTS

| WO | WO 01/10868 | 2/2001 |
| WO | WO 02/100828 | 12/2002 |

OTHER PUBLICATIONS

Almansa et al., Synthesis and SAR of a New Series of COX-2-Selective Inhibitors: Pyrazolo[1,5-*a*]pyrimidines, J. Med. Chem. 2001, 44, pp. 350-361 XP-002330232.
Al-Mousawi[a] et al., Synthesis of New Pyrazolo[1,5-a]pyrimidines And Pyrazolo[3,4-*b*]pyridines 2001, J. Heterocyclic Chem., 38, pp. 989-991 XP002330233.
International Search Report dated Jun. 7, 2005, PCT/US2004/040241.

*Primary Examiner*—James O Wilson
*Assistant Examiner*—Susanna Moore

(57) ABSTRACT

An improved method of making a substituted pyrazolopyrimidine. The method comprises reacting a aminopyrazole compound or a salt thereof with a substituted 1-oxo-2-propenyl-arene(-heterocycle) or a salt thereof under acidic conditions in a reaction medium including a two-phase mixture of an aqueous solution and a water-immiscible organic liquid. Specific substituted pyrazolopyrimidines include N-[3-(3-cyanopyrazolo[1,5-a]pyrimidin-7-yl)phenyl]-N-ethylacetamide and N-methyl-N-(3-{3-[2-thienyl-carbonyl]-pyrazolo[1,5-a]-pyrimidin-7-yl}phenyl)acetamide.

35 Claims, No Drawings

TWO-PHASE METHOD FOR THE SYNTHESIS OF SELECTED PYRAZOLOPYRIMIDINES

CROSS REFERENCE TO RELATED APPLICATIONS

This application is a national stage application of PCT/US2004/040241, filed Dec. 2, 2004, which claims the benefit of U.S. Provisional Application No. 60/536,302, filed Jan. 14, 2004.

FIELD OF THE INVENTION

The present invention relates to a two-phase method for the synthesis of selected pyrazolopyrimidines and relates more specifically to an improved method for the synthesis of N-[3-(3-cyanopyrazolo[1,5-a]pyrimidin-7-yl)phenyl]-N-ethylacetamide.

BACKGROUND OF THE INVENTION

Substituted pyrazolopyrimidines are known as actives for anxiolytic, anticonvulsant, antiepileptic, sedative-hypnotic and skeletal muscle relaxant agents. Illustrative substituted pyrazolopyrimidines include N-[3-(3-cyanopyrazolo[1,5-a]pyrimidin-7-yl)phenyl]-N-ethylacetamide, (hereinafter zaleplon, discussed below), and N-methyl-N-(3-{3-[2-thienyl-carbonyl]pyrazolo[1,5-a]-pyrimidin-7-yl}phenyl)acetamide (herein after Indiplon™, disclosed in U.S. Pat. No. 6,399,621).

Zaleplon is known as having anxiolytic, antiepileptic, sedative and hypnotic properties. The U.S. F.D.A. has approved zaleplon for use for short-term treatment of insomnia. The prior art discloses a method for preparing zaleplon in U.S. Pat. No. 4,626,538, wherein N-(3-acetylphenyl)ethanamide is condensed with dimethylformamide dimethyl acetal to form N-[3-[3-(dimethylamine)-1-oxo-2-propenyl)]phenyl]acetamide. The primary amide of the acetamide is then alkylated with ethyl iodide to form N-[3-[3-(dimethylamino)-1-oxo-2-propenyl]phenyl]-N-ethylacetamide. The ethylacetamide is then condensed with 3-amino-4-cyanopyrazole in refluxing glacial acetic acid for eight hours until the conversion to zaleplon is substantially complete.

U.S. Pat. No. 5,714,607 discloses an improvement over the '538 process for producing zaleplon. It is claimed in the '607 patent that improved yield and purity can be obtained at a faster rate if the final step of the '538 process is modified by adding water to the acetic acid solvent at about 10% to about 85% (v/v). The improved conditions are stated to shorten the reaction time from 3-3.5 to 1-3.5 hours. The improved reaction is said to result in yields ranging from 81.7-90% with purity ranging from 98.77 to 99.4% according to HPLC analysis.

WO 02/100828 A2 discloses a further improvement in the '538 process by reacting the same intermediates, N-[3-[3-(dimethylamino)-1-oxo-2-propenyl]phenyl]-N-ethylacetamide and 3-amino-4-cyanopyrazole, in a liquid medium of water and a water-miscible organic compound under acidic conditions. Although the reaction is claimed to proceed through an imine intermediate that was prone to precipitate from water, the imine intermediate remained dissolved in the reaction media. It is stated in the '828 patent that the process proceeds rapidly at ambient temperature to produce zaleplon with a 91-97% yield having a purity ranging from 98.7 to 99.5% according the HPLC analysis. The method minimized the formation of a regioisomer by-product, N-[3-(3-cyanopyrazolo[1,5-a]pyrimidin-5-yl)phenyl]-N-ethylacetamide which is favored under excess acid conditions.

It is therefore desirable to have an improved process for the preparation of substituted pyrazolopyrimidines that results in near quantitative conversion after a few hours at ambient temperature.

SUMMARY OF THE INVENTION

An aspect of the present invention is to provide an improved method of making a substituted pyrazolopyrimidine compound. The method comprises reacting an aminopyrazole compound or a salt thereof with a substituted 1-oxo-2-propenyl-compound or a salt thereof under acidic conditions in a reaction medium including a two-phase mixture of an aqueous solution and a water-immiscible organic liquid.

This is merely an illustrative aspect of the present invention and should not be deemed an all-inclusive listing of the aspects associated with the present invention. These other aspects will become apparent to those skilled in the art in light of the following disclosure.

DETAILED DESCRIPTION

There is provided a two-phase synthesis of substituted pyrazolopyrimidines resulting in near quantitative conversion at moderate temperatures.

The substituted pyrazolopyrimidines, or pharmaceutically acceptable salts thereof, of the present invention are represented by Formula I:

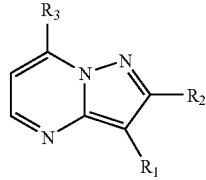

Formula I wherein $R_1$ is selected from the group consisting of hydrogen, fluoro, chloro, bromo, formyl, carboxyl, cyano, hydroxymethyl, N-hydroxyformimidoyl and $R_4CO$— with $R_4$ selected from the group consisting of hydrogen; alkyl($C_1$-$C_6$); alkoxy($C_1$-$C_6$); unsubstituted phenyl; phenyl mono- or disubstituted by halogen, alkyl($C_1$-$C_3$) or alkoxy($C_1$-$C_3$); phenyl ($C_1$-$C_3$), phenyl substituted by trifluoromethyl, alkylthio($C_1$-$C_3$), alkylamino($C_1$-$C_3$), dialkylamino($C_1$-$C_3$), methylenedioxy, alkylsulfonyl($C_1$-$C_3$) or alkanoylamino($C_1$-$C_3$); naphthalenyl; thiazolyl; biphenyl; thienyl; furanyl; pyridinyl; substituted thiazolyl; substituted biphenyl; substituted thienyl; and substituted pyridinyl, wherein the substituents are selected from one or two of the groups consisting of halogen, alkyl($C_1$-$C_3$) and alkoxy($C_1$-$C_3$);

$R_2$ is selected from the group consisting of hydrogen, fluoro, chloro, bromo, cyano, cyanomethyl, carbamoyl and alkyl ($C_1$-$C_3$); and $R_3$ is selected from the group consisting of phenyl; o-trifluoromethylphenyl; m-trifluoromethylphenyl; m-methoxyphenyl, pyridyl, pyridyl N-oxide, thienyl, furanyl, and substituted phenyl wherein one or more of the positions is substituted by a group represented by Formula II

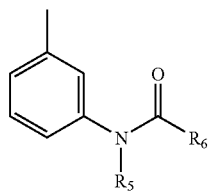

Formula II wherein $R_5$ is selected from the group consisting of hydrogen, alkyl($C_1$-$C_6$), alkenyl($C_2$-$C_6$), alkynyl, cycloalkyl($C_3$-$C_6$)methyl, —$CH_2OCH_3$, —$CH_2CH_2OCH_3$, —$CH_2CH_2OH$, —$CH_2CHOHCH_2OH$, and —$[CH_2CH_2O]_{n=10-120}$; and $R_6$ is selected from the group consisting of alkyl($C_1$-$C_6$), cycloalkyl($C_3$-$C_6$), —O-alkyl($C_1$-$C_6$), —NH-alkyl($C_1$-$C_3$), —N-dialkyl($C_1$-$C_3$), —($CH_2$)nO-alkyl($C_1$-$C_3$), —($CH_2$)$_n$NH-alkyl($C_1$-$C_3$) and —($CH_2$)$_n$N-dialkyl($C_1$-$C_3$), where n is an integer 1 to 3 inclusive.

Illustrative compounds that may be synthesized by the present method include but are not limited to:

N-[3-(3-cyanopyrazolo[1,5-a]pyrimidin-7-yl)phenyl]-N-ethylpropanamide;
N-[3-(3-cyanopyrazolo[1,5-a]pyrimidin-7-yl)phenyl]-N-ethylacetamide;
N-[3-(3-cyanopyrazolo[1,5-a]pyrimidin-7-yl)phenyl]-N-propylacetamide;
N-[3-(3-cyanopyrazolo[1,5-a]pyrimidin-7-yl)phenyl]-N-(polyethyleneglycol)acetamide;
N-[3-(3-cyanopyrazolo[1,5-a]pyrimidin-7-yl)phenyl]-N-(methoxyethyl)acetamide;
N-[3-(3-cyanopyrazolo[1,5-a]pyrimidin-7-yl)phenyl]-N-(hydroxyethyl)acetamide;
N-[3-(3-cyanopyrazolo[1,5-a]pyrimidin-7-yl)phenyl]-N-(1',2'-propanediol)acetamide;
N-[3-(3-cyanopyrazolo[1,5-a]pyrimidin-7-yl)phenyl]-N-(1'-propanol)acetamide;
N-[3-(3-cyanopyrazolo[1,5-a]pyrimidin-7-yl)phenyl]-N-(2'-propanol)acetamide;
[3-(3-cyanopyrazolo[1,5-a]pyrimidin-7-yl)phenyl]methylcarbamic acid, methyl ester;
7-[3-[(methoxycarbonyl)methylamino]phenyl]pyrazolo[1,5-a]pyrimidine-3-carboxylic acid, ethyl ester;
[3-(3-cyanopyrazolo[1,5-a]pyrimidin-7-yl)phenyl]ethylcarbamic acid, methyl ester;
ethyl(3-pyrazolo[1,5-a]pyrimidin-7-ylphenyl)carbamic acid, ethyl ester;
[3-(3-chloropyrazolo[1,5-a]pyrimidin-7-yl)phenyl]ethylcarbamic acid, ethyl ester;
N-[3-(3-cyanopyrazolo[1,5-a]pyrimidin-7-yl)phenyl]-N-2-propenylacetamide;
N-[3-(3-cyanopyrazolo[1,5-a]pyrimidin-7-yl)phenyl]-N-2-propynylacetamide;
N-[3-(3-cyanopyrazolo[1,5-a]pyrimidin-7-yl)phenyl]-N-methylacetamide;
7-(3-pyridyl)pyrazolo[1,5-a]pyrimidine;
7-(3-pyridyl)pyrazolo[1,5-a]pyrimidine-3-carbonitrile;
2-ethyl-7-(3-pyridyl)pyrazolo[1,5-a]pyrimidine-3-carbonitrile;
7-(3-pyridyl)pyrazolo[1,5-a]pyrimidine-3-carboxylic acid ethyl ester;
2-ethyl-7-(3-pyridyl)pyrazolo[1,5-a]pyrimidine-3-carboxylic acid ethyl ester;
7-(3-thienyl)pyrazolo[1,5-a]pyrimidine-3-carboxylic acid ethyl ester;
7-(3-thienyl)pyrazolo[1,5-a]pyrimidine-3-carbonitrile;
6-methyl-7-(3-pyridyl)pyrazolo[1,5-a]pyrimidine-3-carbonitrile;
3-bromo-7-(3-pyridyl)pyrazolo[1,5-a]pyrimidine;
3-chloro-7-(3-pyridyl)pyrazolo[1,5-a]pyrimidine;
7-(3-pyridyl)pyrazolo[1,5-a]pyrimidine, pyridine-1-oxide;
2-methyl-7-(3-pyridyl)pyrazolo[1,5-a]pyrimidine-3-carbonitrile;
2,6-dimethyl-7-(3-pyridyl)pyrazolo[1,5-a]pyrimidine-3-carbonitrile;
2-methyl-7-(3-pyridyl)pyrazolo[1,5-a]pyrimidine-3-carboxylic acid ethyl ester;
N-[3-(3-benzoylpyrazolo[1,5-a]pyrimidin-7-yl)phenyl]-N-methylcyclobutanecarboxamide;
N-[3-(3-benzoylpyrazolo[1,5-a]pyrimidin-7-yl)phenyl]-N-methylcyclopropanecarboxamide;
[3-(3-benzoylpyrazolo[1,5-a]pyrimidin-7-yl)phenyl]methylcarbamic acid, methyl ester;
N-methyl-N-[3-[3-(2-thienylcarbonyl)pyrazolo[1,5-a]pyrimidin-7-yl]phenyl]-cyclopropanecarboxamide;
[3-(3-benzoylpyrazolo[1,5-a]pyrimidin-7-yl)phenyl]methylcarbamic acid, methyl ester;
[3-(3-benzoylpyrazolo[1,5-a]pyrimidin-7-yl)phenyl]ethylcarbamic acid, ethyl ester;
N-2-propenyl-N-[3-[3-(2-thienylcarbonyl)pyrazolo[1,5-a]pyrimidin-7-yl]phenyl]acetamide;
ethyl[3-[3-(2-thienylcarbonyl)pyrazolo[1,5-a]pyrimidin-7-yl]phenyl]carbamic acid, ethyl ester;
N-[3-(3-benzoylpyrazolo[1,5-a]pyrimidin-7-yl)phenyl]-N-2-propenylacetamide;
N-[3-(3-benzoylpyrazolo[1,5-a]pyrimidin-7-yl)phenyl]-N-2-propynylacetamide;
N-methyl-N-(3-{3-[2-thienylcarbonyl]pyrazolo[1,5-a]pyrimidin-7-yl}phenyl)acetamide;
7-(α,α,α-trifluoro-m-tolyl)pyrazolo[1,5-a]pyrimidine-3-carbonitrile;
ethyl 7 (α,α,α-trifluoro-m-tolyl)pyrazolo[1,5-a]pyrimidine-3-carboxylate;
methyl 7-(α,α,α-trifluoro-m-tolyl)pyrazolo[1,5-a]pyrimidin-3-yl ketone;
7-(α,α,α-trifluoro-m-tolyl)pyrazolo[1,5-a]pyrimidine-3-carboxaldehyde oxime;
7-(m-methoxyphenyl)pyrazolo[1,5-a]pyrimidine-3-carbonitrile;
3-(methoxymethyl)-7-(α,α,α-trifluoro-m-tolyl)pyrazolo[1,5-a]pyrimidine;
3-bromo-7-(α,α,α-trifluoro-m-tolyl)pyrazolo[1,5-a]pyrimidine;
2-cyano-7(α,α,α-trifluoro-m-tolyl)pyrazolo[1,5-a]pyrimidine-3-carbonitrile;
3-cyano-7-(α,α,α-trifluoro-m-tolyl)pyrazolo[1,5-a]-pyrimidine-2-acetonitrile;
3-methyl-7-(α,α,α-trifluoro-m-tolyl)pyrazolo[1,5-a]pyrimidine;
ethyl 7-(m-tolyl)pyrazolo[1,5-a]pyrimidine-3-carboxylate;
ethyl 7-(3,4-xylyl)pyrazolo[1,5-a]pyrimidine-3-carboxylate;
ethyl 7-(p-ethylphenyl)pyrazolo[1,5-a]pyrimidine-3-carboxylate;
ethyl 7-(3,4-dimethoxyphenyl)pyrazolo[1,5-a]pyrimidine-3-carboxylate;
7-(m-fluorophenyl)pyrazolo[1,5-a]pyrimidine-3-carbonitrile;
5-phenylpyrazolo[1,5-a]pyrimidine; and
5-(α,α,α-trifluoro-m-tolyl)pyrazolo[1,5-a]pyrimidine.

The substituted pyrazolopyrimidines according to Formula I are synthesized by the reaction of a pyrazole compound according the Formula III or a salt thereof with a substituted 1-oxo-2-propenyl-arene(heterocycle) compound according to Formula IV or a salt thereof, both illustrated below:

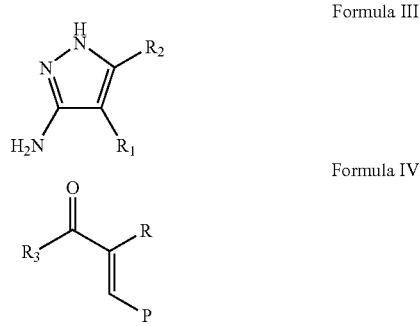

Formula III

Formula IV wherein $R_1$ is selected from the group consisting of hydrogen, fluoro, chloro, bromo, formyl, carboxyl, cyano, hydroxymethyl, N-hydroxyformimidoyl and $R_4CO$—, wherein $R_4$ is selected from the group consisting of hydrogen, alkyl($C_1$-$C_6$), alkoxy($C_1$-$C_6$), unsubstituted phenyl; phenyl mono- or disubstituted halogen, alkyl($C_1$-$C_3$) or alkoxy($C_1$-$C_3$); phenyl ($C_1$-$C_3$), phenyl substituted by trifluoromethyl, alkylthio($C_1$-$C_3$), alkylamino($C_1$-$C_3$), dialkylamino($C_1$-$C_3$), methylenedioxy, alkylsulfonyl($C_1$-$C_3$) or alkanoylamino($C_1$-$C_3$); naphthalenyl; thiazolyl; biphenyl; thienyl; furanyl; pyridinyl; substituted thiazolyl; substituted biphenyl; substituted thienyl; and substituted pyridinyl, wherein the substituents are selected from one or two of the groups consisting of halogen, alkyl($C_1$-$C_3$) and alkoxy($C_1$-$C_3$);

wherein $R_2$ is selected from the group consisting of hydrogen, fluoro, chloro, bromo, cyano, cyanomethyl, carbamoyl or alkyl ($C_1$-$C_3$); and wherein $R_3$ is a group such as phenyl; o-trifluoromethylphenyl; m-trifluoromethylphenyl; m-methoxyphenyl, substituted pyridyl, pyridyl N-oxide, thienyl, furanyl or represented by Formula II

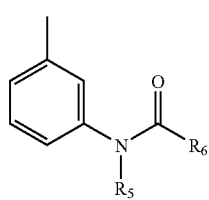

Formula II wherein $R_5$ is selected from the group consisting of hydrogen, alkyl($C_1$-$C_6$), alkenyl($C_2$-$C_6$), alkynyl, cycloalkyl($C_3$-$C_6$)methyl, —$CH_2OCH_3$, —$CH_2CH_2OCH_3$, —$CH_2CH_2OH$, —$CH_2CHOHCH_2OH$, and —$[CH_2CH_2O]_{n=10\text{-}120}$;

$R_6$ is selected from the group consisting of alkyl($C_1$-$C_6$), cycloalkyl($C_3$-$C_6$), —O-alkyl($C_1$-$C_6$), —NH-alkyl($C_1$-$C_3$), —N-dialkyl($C_1$-$C_3$), —($CH_2$)$_n$O-alkyl($C_1$-$C_3$), —($CH_2$)$_n$NH-alkyl($C_1$-$C_3$) and —($CH_2$)$_n$N-dialkyl($C_1$-$C_3$), where n is an integer 1 to 3 inclusive;

P is selected from the group consisting of —OAc, —OR, —SR and —NR'R; and

R and R' are selected from the group consisting of hydrogen, alkyl($C_1$-$C_6$) and cyclic alkyl.

The reaction of Formula III or a salt thereof with Formula IV or a salt thereof takes place under acidic conditions in a reaction medium comprising a two-phase mixture of an aqueous solution and a water-immiscible organic liquid at about room temperature.

The reaction medium may contain a phase-transfer agent to facilitate the reaction rate. Suitable phase-transfer agents include but are not limited to the following: Aliquat® 336, ALKANOL®s, Polyethylene(PEG) esters and diesters, polypropylene glycol (PPG) and PEG-PPG copolymers, tetraalkylammonium salts, tetraalkylphosphonium salts, N-alkylpyridinium salts, sodium stearate, sodium palmitate, sodium laurate. Although the reaction medium can under some circumstances form a microemulsion or emulsion, two phases that separate quickly on settling are preferred.

The aqueous solution phase includes but is not limited to water including a dissolved acid. The aqueous solution may include at least one water miscible solvent or polymer selected from the group consisting of formamide, acetamide, 1-methyl-2-pyrrolidinone, DMF, DMAC, DMSO, hexamethylphosphoramide, hexamethylphosphortriamide, methylsulfone, sulfolane, 1-methylpropandiol, methanol, ethanol, propanol, butanol, acetonitrile, propionitrile, THF, glycol ethers, acetone, dioxane, nitromethane, nitroethane, polyethylene glycol, polyoxyethylene, polyglycerol, polyvinylpyrrolidone, polyvinyl alcohol and mixtures thereof.

Water-soluble salts may be added to the aqueous solution to reduce product losses to the aqueous phase. These salts may include a salt selected from the group consisting of sodium chloride, sodium bromide, sodium sulfate, sodium hydrogen phosphate, sodium dihydrogen phosphate, sodium phosphate, sodium acetate, ammonium acetate, sodium tartrate, sodium benzoate, sodium phthalate and mixtures thereof.

The aqueous immiscible phase may include an organic liquid selected from the group consisting of chloroform, dichloromethane, hexane and hexane compounds, heptane, cyclohexane, methylcyclohexane, anisole, fluorobenzene, chlorobenzene, toluene, xylene and xylene compounds, diethylether, tert-butylmethylether, n-propyl formate, ethyl acetate, butyl acetate, propyl acetate, isoamyl acetate, 2-butanone, 2-hexanone, 3-methyl-2-pentanone, 4-methyl-2-pentanone, pinacolone, 2-heptanone, acetophenone, cyclohexanone, cyclopentanone, long-chained alcohols, for example; decanol, dodecanol and mixtures thereof.

The condensation reaction in general requires one equivalent of an acid unless the acid salts of either or both of the two reactants are used, as is well known in the art. Suitable acids include mineral acids, organic acids and mixtures thereof. Acceptable mineral and organic acids may include at least one acid selected from the group consisting of hydrochloric, hydrobromic, hydrofluoric sulfuric, acetic, formic, methanesulfonic, p-toluenesulfonic, trifluoroacetic, hexanesulfonic, heptafluorobutyric, perchloric, nitric, phosphoric acid and mixtures thereof.

An illustrative advantage of the present invention over the prior art is that upon completion of the reaction the product is easily separated by removing the product-containing organic phase from the aqueous phase containing the remaining reactants. After conventional solvent removal and recovery, the product is usually of acceptable purity. However, the product may be crystallized from the organic phase solvent by concentrating and cooling. The method of the present invention has the advantage that problematic regioisomers are only produced in trace quantities in the environment of the reaction medium.

An illustrative use of the present invention is the production of zaleplon, wherein an analog of Formula IV is N-[3-[3-(dimethylamino)-1-oxo-2-propenyl]phenyl]-N-ethylacetamide and an analog of Formula III is 3-amino-4-cyanopyrazole. The N-[3-[3-(dimethylamino)-1-oxo-2-propenyl]phenyl]-N-ethylacetamide is reacted with the 3-amino-4-cyanopyrazole under acidic conditions in a reaction medium comprising a two-phase mixture of an aqueous solution and a water-immiscible organic liquid at about room temperature, according to the present invention as discussed above. An unexpectedly preferred water immiscible organic liquid is one that includes methylethylketone, 2-butanone. It would be expected that the 3-amino-4-cyanopyrazole would be consumed by a reaction with 2-butanone to form a Schiff's base, but this is not observed when one equivalent of acid is used.

The product optionally may be crystallized from the organic phase solvent. An improvement is that in the production of zaleplon by the present invention the problematic regioisomer, N-[3-(3-cyanopyrazolo[1,5-a]pyrimidin-5-yl)phenyl]-N-ethylacetamide, described in the prior art above, is only formed in trace quantities in the environment of the reaction medium.

Another illustrative use of the present invention is the production of Indiplon™ wherein an analog of Formula IV is N-[3-[3-(dimethylamino)-1-oxo-2-propenyl]phenyl]-N-methylacetamide and is reacted with an analog of Formula III, (3-amino-1H-pyrazol-4-yl)-2-thienylmethanone under acidic conditions in a reaction medium comprising a two-phase mixture of an aqueous solution and a water-immiscible organic liquid at about room temperature, according to the present invention as discussed above. Typically, one equivalent of acid is used. The product optionally may be crystallized from the organic phase solvent.

The following examples are given for the purposes of illustration only and are not intended to be limiting of the present invention in any way.

EXAMPLE 1

N-[3-[3-(dimethylamino)-1-oxo-2-propenyl]phenyl]-N-ethylacetamide (1.3 g) and 3-amino-4-cyanopyrazole (0.54 g) were weighed into a 50 mL Erlenmeyer flask containing a magnetic stir bar. Water (17 mL), 2-butanone (15 mL) and 37% HCl (0.5 mL) were added to form the two-phase mixture. The two-phase mixture was stirred vigorously at room temperature and sampled for HPLC (50 μL each phase/100 mL methanol) at 30 minutes, 60 minutes, 90 minutes and after stirring overnight. The area percents for zaleplon were 39.5% 71.2% 81.7% and 100% at the stated time intervals, respectively.

EXAMPLE 2

N-[3-[3-(dimethylamino)-1-oxo-2-propenyl]phenyl]-N-ethylacetamide (1.3 g), 3-amino-4-cyanopyrazole (0.54 g) were weighed into a 50 mL Erlenmeyer flask containing a magnetic stir bar. Water (17 mL), 2-butanone (17 mL) and of heptafluorobutyric acid (0.5 mL) were added to form the two phases. The two-phase mixture was stirred vigorously at room temperature and sampled for HPLC (50 μL each phase/100 mL methanol) at 30 minutes, 60 minutes, 90 minutes, and after stirring overnight. The area percents for zaleplon were 55.0%, 77.5%, 86.7% and 100% at the stated time intervals, respectively.

EXAMPLE 3

The reaction of Example 1 was repeated using (3-amino-1H-pyrazol-4-yl)-2-thienylmethanone in place of the and N-[3-[3-(dimethylamino)-1-oxo-2-propenyl]phenyl]-N-methylacetamide as reactants, wherein the product is Indiplon™.

EXAMPLE 4

Procedure to Prepare a Kilogram of Zaleplon

N-[3-(3-Dimethylamino-1-oxo-2-propenyl)phenyl]-N-ethylacetamide (1001 g, 3.85 mol), 3-amino-4-cyanopyazole (422 g, 3.90 mol), 2-butanone (5.77 L, 4.64 kg) and water (5.77 L) were added to a glass reactor equipped with temperature control, stirring and nitrogen sweep. The resulting reaction mixture was stirred at about 25-30° C. until the solids were substantially dissolved. Hydrochloric acid (325 mL; 390 g) was diluted with water (1.86 L) and added in 4 equal portions over a one-hour period to the reaction mixture. The resulting reaction mixture was stirred for 1 to 2 hours at 25-35° C. The reaction mixture was then heated to boiling. Approximately 4.65 L of volatiles were taken off until the pot temperature reached 79-80° C.

Water (1.86 L) was added and the reaction mixture was cool to 25-40° C. The cooled reaction mixture was filtered. The resulting cake was washed with water (3.7 L). The remaining solids were dried at 90° C.

The crude zaleplon weighed 1073 g for a 92.5% yield.

The crude zaleplon was combined with ethanol (5.365 L) and water (0.536 L) in a glass vessel and heated to reflux at about 80° C. The resulting mixture was filtered to remove insoluble materials and then washed with ethanol (0.1 L). The filtrate was combined with the wash liquor and resuspended with stirring at 5-10° C. for about one hour. The product was separated by filtration. The filtrate was washed with a 50:50 solution of ethanol and water (1 L). The solids were dried at 90° C. yielding about 1 kg of zaleplon.

HPLC Results:

| Sample | Assay w/w | N-Me Zal. % a | RI IMP % a | MW 520 % a |
| --- | --- | --- | --- | --- |
| CRUDE | * | 0.20 | 0.15 | 0.18 |
| PURIFIED | 101.4% | 0.21 | 0.07 | 0.23 |

* Assay was not run.

The invention claimed is:

1. A method of making a substituted pyrazolopyrimidine, or pharmaceutically acceptable salt thereof, wherein the substituted pyrazolopyrimidine is a compound of Formula I,

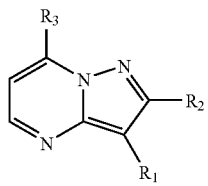

Formula I wherein
- R$_1$ is selected from the group consisting of hydrogen, fluoro, chloro, bromo, formyl, carboxyl, cyano, hydroxymethyl, N-hydroxyformimidoyl and R$_4$CO— wherein R$_4$ is selected from the group consisting of hydrogen; alkyl(C$_1$-C$_6$); alkoxy(C$_1$-C$_6$); unsubstituted phenyl; phenyl mono- or disubstituted by halogen, alkyl (C$_1$-C$_3$) or alkoxy(C$_1$-C$_3$); phenyl, phenyl substituted by trifluoromethyl, alkylthio(C$_1$-C$_3$), alkylamino(C$_1$-C$_3$), dialkylamino(C$_1$-C$_3$), methylenedioxy, alkylsulfonyl (C$_1$-C$_3$) or alkanoylamino(C$_1$-C$_3$); naphthalenyl; thiazolyl; biphenyl; thienyl; furanyl; pyridinyl; substituted thiazolyl; substituted biphenyl; substituted thienyl; and substituted pyridinyl, wherein the substituents are selected from one or two of the groups consisting of halogen, alkyl(C$_1$-C$_3$) and alkoxy(C$_1$-C$_3$);
- R$_2$ is selected from the group consisting of hydrogen, fluoro, chloro, bromo, cyano, cyanomethyl, carbamoyl or alkyl (C$_1$-C$_3$); and
- R$_3$ is selected from the group consisting of phenyl; o-trifluoromethylphenyl; m-trifluoromethylphenyl; m-methoxyphenyl; pyridyl; pyridyl N-oxide; thienyl; furanyl; and substituted phenyl, wherein one or more of the positions is substituted by a group represented by Formula II

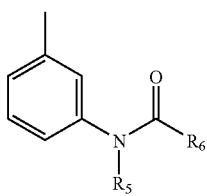

Formula II wherein
- R$_5$ is selected from the group consisting of hydrogen, alkyl (C$_1$-C$_6$), alkenyl(C$_2$-C$_6$), alkynyl, cycloalkyl(C$_3$-C$_6$) methyl, —CH$_2$OCH$_3$, —CH$_2$CH$_2$OCH$_3$, —CH$_2$CH$_2$OH, —CH$_2$CHOHCH$_2$OH, and —[CH$_2$CH$_2$O]$_{n=10\text{-}120}$; and
- R$_6$ is selected from the group consisting of alkyl(C$_1$-C$_6$), cycloalkyl(C$_3$-C$_6$), —O-alkyl(C$_1$-C$_6$), —NH-alkyl(C$_1$-C$_3$), —N-dialkyl(C$_1$-C$_3$), —(CH$_2$)$_n$O-alkyl(C$_1$-C$_3$), —(CH$_2$)$_n$NH-alkyl(C$_1$-C$_3$) and —(CH$_2$)$_n$N-dialkyl(C$_1$-C$_3$), where n is an integer 1 to 3 inclusive;

the method comprising reacting an aminopyrazole compound or a salt thereof with a substituted 1-oxo-2-propenyl-compound or a salt thereof under acidic conditions in a reaction medium including a two-phase mixture of an aqueous solution and a water-immiscible organic liquid.

2. The method of claim 1 wherein the reaction mixture further includes at least one phase-transfer agent.

3. The method of claim 1 wherein the aqueous phase includes a water-soluble salt.

4. The method of claim 3 wherein the water soluble salt includes a salt selected from the group consisting of sodium chloride, sodium bromide, sodium sulfate, sodium hydrogen phosphate, sodium dihydrogen phosphate, sodium phosphate, sodium acetate, ammonium acetate, sodium tartrate, sodium benzoate, sodium phthalate and mixtures thereof.

5. The method of claim 1 wherein the acidic conditions are prepared by the addition of at least one acid selected from the group consisting of at least one mineral acid, at least one organic acid and mixtures thereof.

6. The method of claim 5 wherein the at least one add includes an acid selected from the group consisting of hydrochloric, hydrobromic, hydrofluoric, sulfuric, acetic, formic, methanesulfonic, p-toluenesulfonic, trifluoroacetic, hexanesulfonic, heptafluorobutyric, perchloric, nitric, phosphoric acid and mixtures thereof.

7. The method of claim 1 wherein the aqueous phase includes water.

8. The method of claim 1 wherein the aqueous phase includes at least one water miscible solvent or polymer selected from the group consisting of formamide, acetamide, 1-methyl-2-pyrrolidinone, dimethylformamide (DMF), dimethylacetamide (DMAC), dimethylsulfoxide (DMSO), hexamethylphosphoramide, hexamethylphosphortriamide, methylsulfone, sulfolane, 1-methylpropandiol, methanol, ethanol, propanol, butanol, acetonitrile, propionitrile, tetrahydrofuran (THF), glycol ethers, acetone, dioxane, nitromethane, nitroethane, polyethylene glycol, polyoxyethylene, polyglycerol, polyvinylpyrrolidone, polyvinyl alcohol and mixtures thereof.

9. The method of claim 1 wherein the water immiscible organic liquid includes an organic liquid selected from the group consisting of chloroform, dichloromethane, hexane heptane, cyclohexane, methylcyclohexane, anisole, fluorobenzene, chlorobenzene, toluene, xylene, diethylether, tert-butylmethylether, n-propyl formate, ethyl acetate, butyl acetate, propyl acetate, isoamyl acetate, 2-butanone, 2-hexanone, 3-methyl-2-pentanone, 4-methyl-2-pentanone, pinacolone, 2-heptanone, acetophenone, cyclohexanone, cyclopentanone, long-chained alcohols, and mixtures thereof.

10. The method of claim 1 further including extracting the substituted pyrazolopyrimidine from the water immiscible organic liquid.

11. The method of claim 10 further including recrystallizing the extracted, substituted pyrazolopyrimidine.

12. The method of claim 2 wherein the at least one phase transfer agent is selected from the group consisting of: polyethylene glycol (PEG) esters and diesters, polypropylene glycol (PPG) and PEG-PPG copolymers, tetraalkylammonium salts, tetraalkylphosphonium salts, N-alkylpyridinium salts, sodium stearate, sodium palmitate, sodium laurate.

13. The method of claim 1 wherein Formula I is selected from the group consisting of:
- N-[3-(3-cyanopyrazolo[1,5-a]pyrimidin-7-yl)phenyl]-N-ethylpropanamide;
- N-[3-(3-cyanopyrazolo[1,5-a]pyrimidin-7-yl)phenyl]-N-ethylacetamide;
- N-[3-(3-cyanopyrazolo[1,5-a]pyrimidin-7-yl)phenyl]-N-propylacetamide;
- N-[3-(3-cyanopyrazolo[1,5-a]pyrimidin-7-yl)phenyl]-N-(polyethyleneglycol)acetamide;
- N-[3-(3-cyanopyrazolo[1,5-a]pyrimidin-7-yl)phenyl]-N-(methoxyethyl)acetamide;
- N-[3-(3-cyanopyrazolo[1,5-a]pyrimidin-7-yl)phenyl]-N-(hydroxyethyl)acetamide;

N-[3-(3-cyanopyrazolo[1,5-a]pyrimidin-7-yl)phenyl]-N-(1',2'-propanediol)acetamide;
N-[3-(3-cyanopyrazolo[1,5-a]pyrimidin-7-yl)phenyl]-N-(1'-propanol)acetamide;
N-[3-(3-cyanopyrazolo[1,5-a]pyrimidin-7-yl)phenyl]-N-(2'-propanol)acetamide;
[3-(3-cyanopyrazolo[1,5-a]pyrimidin-7-yl)phenyl]methylcarbamic acid, methyl ester;
7-[3-[(methoxycarbonyl)methylamino]phenyl]pyrazolo[1,5-a]pyrimidine-3-carboxylic acid, ethyl ester;
[3-(3-cyanopyrazolo[1,5-a]pyrimidin-7-yl)phenyl]ethylcarbamic acid, methyl ester;
ethyl(3-pyrazolo[1,5-a]pyrimidin-7-ylphenyl)carbamic acid, ethyl ester;
[3-(3-chloropyrazolo[1,5-a]pyrimidin-7-yl)phenyl]ethylcarbamic acid, ethyl ester;
N-[3-(3-cyanopyrazolo[1,5-a]pyrimidin-7-yl) phenyl]-N-2-propenylacetamide;
N-[3-(3-cyanopyrazolo[1,5-a]pyrimidin-7-yl) phenyl]-N-2-propynylacetamide;
N-[3-(3-cyanopyrazolo[1,5-a]pyrimidin-7-yl) phenyl]-N-methylacetamide;
7-(3-pyridyl)pyrazolo[1,5-a]pyrimidine;
7-(3-pyridyl)pyrazolo[1,5-a]pyrimidine-3-carbonitrile;
2-ethyl-7-(3-pyridyl)pyrazolo[1,5-a]pyrimidine-3-carbonitrile;
7-(3-pyridyl)pyrazolo[1,5-a]pyrimidine-3-carboxylic acid ethyl ester;
2-ethyl-7-(3-pyridyl)pyrazolo[1,5-a]pyrimidine-3-carboxylic acid ethyl ester;
7-(3-thienyl)pyrazolo[1,5-a]pyrimidine-3-carboxylic acid ethyl ester;
7-(3-thienyl)pyrazolo[1,5-a]pyrimidine-3-carbonitrile;
6-methyl-7-(3-pyridyl)pyrazolo[1,5-a]pyrimidine-3-carbonitrile;
3-bromo-7-(3-pyridyl)pyrazolo[1,5-a]pyrimidine;
3-chloro-7-(3-pyridyl)pyrazolO[1,5-a]pyrimidine;
7-(3-pyridyl)pyrazolo[1,5-a]pyrimidine, pyridine-1-oxide;
2-methyl-7-(3-pyridyl)pyrazolo[1,5-a]pyrimidine-3-carbonitrile;
2,6-dimethyl-7-(3-pyridyl)pyrazolo[1,5-a]pyrimidine-3-carbonitrile;
2-methyl-7-(3-pyridyl)pyrazolo[1,5-a]pyrimidine-3-carboxylic acid ethyl ester;
N-[3-(3-benzoylpyrazolo[1,5-a]pyrimidin-7-yl)phenyl]-N-methylcyclobutanecarboxamide;
N-[3-(3-benzoylpyrazolo[1,5-a]pyrimidin-7-yl)phenyl]-N-methylcyclopropanecarboxamide;
[3-(3-benzoylpyrazolo[1,5-a]pyrimidin-7-yl)phenyl]methylcarbamic acid, methyl ester;
N-methyl-N-[3-[3-(2-thienylcarbonyl)pyrazolo[1,5-a]pyrimidin-7-yl]phenyl]-cyclopropanecarboxamide;
[3-(3-benzoylpyrazolo]1,5-a]pyrimidin-7-yl)phenyl]methylcarbamic acid, methyl ester;
[3-(3-benzoylpyrazolo[1,5-a]pyrimidin-7-yl)phenyl]ethylcarbamic acid, ethyl ester;
N-2-propenyl-N-[3-[3-(2-thienylcarbonyl)pyrazolo[1,5-a]pyrimidin-7-yl]phenyl]acetamide;
ethyl [3-[3-(2-thienylcarbonyl)pyrazolo[1,5-a]pyrimidin-7-yl]phenyl]carbamic acid, ethyl ester;
N-[3-(3-benzoylpyrazolo[1,5-a]pyrimidin-7-yl)phenyl]-N-2-propenylacetamide;
N-[3-(3-benzoylpyrazolo[1,5-a]pyrimidin-7-yl)phenyl]-N-2-propynylacetamide;
N-methyl-N-(3-{3-[2-thienylcarbonyl]pyrazolo[1,5-a]pyrimidin-7-yl}phenyl)acetamide;
7-($\alpha,\alpha,\alpha$trifluoro-m-tolyl)pyrazolo[1,5-a]pyrimidine-3-carbonitrile;
ethyl 7-($\alpha,\alpha,\alpha$trifluoro-m-tolyl)pyrazolo[1,5-a]pyrimidine-3-carboxylate;
methyl 7-($\alpha,\alpha,\alpha$trifluoro-m-tolyl)pyrazolo[1,5-a]pyrimidin-3-yl ketone;
7-($\alpha,\alpha,\alpha$trifluoro-m-tolyl)pyrazolo[1,5-a]pyrimidine-3-carboxaldehyde oxime;
7-(m-methoxyphenyl)pyrazolol[1,5-a]pyrimidine-3-carbonitrile;
3-(methoxymethyl)-7-($\alpha,\alpha,\alpha$trifluoro-m-tolyl)pyrazolo-[1,5-a]pyrimidine;
3-bromo-7-($\alpha,\alpha,\alpha$trifluoro-m-tolyl)pyrazolo-[1,5-a]pyrimidine;
2-cyano-7-($\alpha,\alpha,\alpha$trifluoro-m-tolyl)pyrazolo[1,5-a]pyrimidine-3-carbonitrile;
3-cyano-7-($\alpha,\alpha,\alpha$trifluoro-m-tolyl)pyrazolo[1,5-a]-pyrimidine-2-acetonitrile;
3-methyl-7-($\alpha,\alpha,\alpha$trifluoro-m-tolyl)pyrazolo[1,5-a]pyrimidine;
ethyl 7-(m-tolyl)pyrazolo[1,5-a]pyrimidine-3-carboxylate;
ethyl 7-(3,4-xylyl)pyrazolo[1,5-a]pyrimidine-3-carboxylate;
ethyl 7-(p-ethylphenyl)pyrazolo[1,5-a]pyrimidine-3-carboxylate;
ethyl 7-(3,4-dimethoxyphenyl)pyrazolo[1,5-a]pyrimidine-3-carboxylate;
7-(m-Fluorophenyl)pyrazolo[1,5-a]pyrimidine-3-carbonitrile;
5-Phenylpyrazolo[1,5-a]pyrimidine; and
5-($\alpha,\alpha,\alpha$-Trifluoro-m-tolyl)pyrazolo[1,5-a]pyrimidine.

14. The method of claim 1, wherein the substituted pyrazolopyrimidine is N-(3-(3-cyanopyrazolo[1,5-a]-pyrimidin-7-yl)phenyl)-N-ethylacetamide, and further wherein the method comprises:

reacting N-[3-[3-(dimethylamino)-1-oxo-2-propenyl]phenyl]-N-ethylacetamide with 3-amino-4-cyanopyrazole under acidic conditions in a reaction medium including a two-phase mixture of an aqueous solution and a water-immiscible organic liquid.

15. The method of claim 14 wherein the reaction mixture further includes at least one phase transfer agent selected from the group consisting of, polyethylene glycol (PEG) esters and diesters, polypropylene glycol (PPG) and PEG-PPG copolymers, tetraalkylammonium salts, tetraalkylphosphonium salts, N-alkylpyridinium salts, sodium stearate, sodium palmitate, sodium laurate.

16. The method of claim 14 wherein the aqueous phase includes a water soluble salt selected from the group consisting of sodium chloride, sodium bromide, sodium sulfate, sodium hydrogen phosphate, sodium dihydrogen phosphate, sodium phosphate, sodium acetate, ammonium acetate, sodium tartrate, sodium benzoate, sodium phthalate and mixtures thereof.

17. The method of claim 14 wherein the acidic conditions are prepared by the addition of at least one acid including an acid selected from the group consisting of at least one mineral acid, at least one organic acid and mixtures thereof.

18. The method of claim 17 wherein the at least one acid includes at least one acid selected from the group consisting of hydrochloric, hydrobromic, hydrofluoric, sulfuric, acetic, formic, methanesulfonic, p-toluenesulfonic, trifluoroacetic, hexanesulfonic, heptafluorobutyric, perchloric, nitric, phosphoric acid and mixtures thereof.

19. The method of claim 14 wherein the aqueous phase includes water.

20. The method of claim 14 wherein the aqueous phase includes at least one water miscible solvent or polymer selected from the group consisting of formamide, acetamide, 1-methyl-2-pyrrolidinone, dimethylformamide (DMF), dimethylacetamide (DMAC), dimethylsulfoxide (DMSO), hexamethyiphosphoramide, hexamethyiphosphoririamide, methylsulfone, sulfolane, 1-methylpropandiol, methanol, ethanol, propanol, butanol, acetonitrile, propionitrile, tetrahydrofuran (THF), glycol ethers, acetone, dioxane, nitromethane, nitroethane, polyethylene glycol, polyoxyethylene, polyglycerol, polyvinylpyrrolidone, polyvinyl alcohol and mixtures thereof.

21. The method of claim 14 wherein the water immiscible organic liquid includes an organic liquid selected from the group consisting of chloroform, dichloromethane, hexane, heptane, cyclohexane, methylcyclohexane, anisole, fluorobenzene, chlorobenzene, toluene, xylene, diethylether, tert-butylmethylether, n-propyl formate, ethyl acetate, butyl acetate, propyl acetate, isoamyl acetate, 2-butanone, 2-hexanone, 3-methyl-2-pentanone, 4-methyl-2-pentanone, pinacolone, 2-heptanone, acetophenone, cyclohexanone, cyclopentanone, long-chained alcohols, and mixtures thereof.

22. The method of claim 14 further including extracting the N-(3-(3-cyanopyrazolol[1,5a]-pyrimidin-7-yl)phenyl)-N-ethylacetamide from the water immiscible organic liquid.

23. The method of claim 22 further including recrystallizing the extracted N-(3-3-cyanopyrazolo[1,5-a]-pyrimidin-7-phenyl)-N-ethylacetamide.

24. The method of claim 1, wherein the substituted pyrazolopyrimidine is N-methyl-N-[3-[3-[2-thienylcarbonyl]pyrazolo[5,1-a]-pyrimidin-7-yl]phenyl]acetamide, and further wherein the method comprises:
reacting N-[3-[3-(dimethylamino)-1-oxo-2-propenyl]phenyl]-N-methylacetamide with (3-amino-1H-pyrazol-4-yl)-2-thienylmethanone under acidic conditions in a reaction medium including a two-phase mixture of an aqueous solution and a water-immiscible organic liquid.

25. The method of claim 24 wherein the reaction mixture further includes at least one phase transfer agent selected from the group consisting of polyethylene glycol (PEG) esters and diesters, polypropylene glycol (PPG) and PEG-PPG copolymers, tetraalkylammonium salts, tetraalkylphosphonium salts, N-alkylpyridinium salts, sodium stearate, sodium palmitate, sodium laurate.

26. The method of claim 24 wherein the aqueous phase includes a water soluble salt selected from the group consisting of sodium chloride, sodium bromide, sodium sulfate, sodium hydrogen phosphate, sodium dihydrogen phosphate, sodium phosphate, sodium acetate, ammonium acetate, sodium tartrate, sodium benzoate, sodium phthalate and mixtures thereof.

27. The method of claim 24 wherein the acidic conditions are prepared by the addition of at least one acid including an acid selected from the group consisting of at least one mineral acid, at least one organic add and mixtures thereof.

28. The method of claim 27 wherein the at least one acid includes at least one acid selected from the group consisting of hydrochloric, hydrobromic, hydrofluoric, sulfuric, acetic, formic, methanesulfonic, p-toluenesulfonic, trifluoroacetic, hexanesulfonic, heptafluorobutyric, perchioric, nitric, phosphoric acid and mixtures thereof.

29. The method of claim 24 wherein the aqueous phase includes water.

30. The method of claim 24 wherein the aqueous phase includes at least one water miscible solvent selected from the group consisting of formamide, acetamide, 1-methyl-2-pyrrolidinone, dimethylformamide (DMF), dimethylacetamide (DMAC), dimethylsulfoxide (DMSO), hexamethylphosphoramide, hexamethylphosphortriamide, methylsulfone, sulfolane, 1-methylpropandiol, methanol, ethanol, propanol, butanol, acetonitrile, propionitrile, tetrahydrofuran (THF), glycol ethers, acetone, dioxane, nitromethane, nitroethane, polyethylene glycol, polyoxyethylene, polyglycerol, polyvinylpyrrolidone, polyvinyl alcohol and mixtures thereof.

31. The method of claim 24 wherein the water immiscible organic liquid includes an organic liquid selected from the group consisting of chloroform, dichloromethane, hexane, heptane, cyclohexane, methylcyclohexane, anisole, fluorobenzene, chlorobenzene, toluene, xylene, diethylether, tert-butylmethylether, n-propyl formate, ethyl acetate, butyl acetate, propyl acetate, isoamyl acetate, 2-butanone, 2-hexanone, 3-methyl-2-pentanone, 4-methyl-2-pentanone, pinacolone, 2-heptanone, acetophenone, cyclohexanone, cyclopentanone, long-chained alcohols, and mixtures thereof.

32. The method of claim 24 further including extracting N-methyl-N-[3-[3-[2-thienylcarbonyl]pyrazolo[5,1-a]-pyrimidin-7-yl]phenyl]acetamide from the water immiscible organic liquid.

33. The method of claim 24 further including recrystallizing the extracted N-methyl-N-[3-[3-[2-thienylcarbonyl]pyrazolo[5,1-a]-pyrimidin-7-yl]phenyl]acetamide.

34. The method of claim 1, wherein the aminopyrazole compound comprises a compound of Formula III:

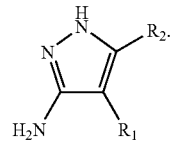

Formula III

35. The method of claim 1, wherein the substituted 1-oxo-2-propenyl-compound comprises a compound of Formula IV:

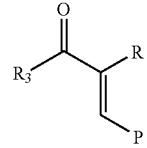

Formula IV wherein P is selected from the group consisting of —OAc, —OR, —SR and —NR'R; and R and R' are selected from the group consisting of hydrogen, alkyl($C_{1-C6}$) and cyclic alkyl.

* * * * *